(12) United States Patent
Fagan et al.

(10) Patent No.: US 9,675,448 B2
(45) Date of Patent: Jun. 13, 2017

(54) SPEECH VALVE, A TOOL FOR FACILITATING INSERTION OF A SPEECH VALVE AND A TOOL FOR HOLDING A SPEECH VALVE

(75) Inventors: Michael Fagan, Brandesburton (GB); Jean Marie Steeve Lamvohee, Beverley (GB); Catherine Dobson, Hull (GB)

(73) Assignee: THE UNIVERSITY OF HULL, Hull (GB)

( * ) Notice: Subject to any disclaimer, the term of this patent is extended or adjusted under 35 U.S.C. 154(b) by 0 days.

(21) Appl. No.: 13/505,065

(22) PCT Filed: Oct. 22, 2010

(86) PCT No.: PCT/EP2010/065951
§ 371 (c)(1),
(2), (4) Date: Apr. 30, 2012

(87) PCT Pub. No.: WO2011/051177
PCT Pub. Date: May 5, 2011

(65) Prior Publication Data
US 2012/0215306 A1   Aug. 23, 2012

(30) Foreign Application Priority Data

Oct. 29, 2009  (GB) .................................. 0918995.2

(51) Int. Cl.
*A61F 11/00* (2006.01)
*A61F 2/20* (2006.01)
(Continued)

(52) U.S. Cl.
CPC .......... *A61F 2/203* (2013.01); *A61B 17/3468* (2013.01); *A61B 17/24* (2013.01)

(58) Field of Classification Search
CPC ..... A61B 17/3468; A61B 17/24; A61F 2/203; A61F 2/20; A61F 2002/206;
(Continued)

(56) References Cited

U.S. PATENT DOCUMENTS 4,465,482 A * 8/1984 Tittel .................... A61M 27/00
                                                              604/523
4,596,579 A *  6/1986 Pruitt ............................... 623/9
(Continued)

FOREIGN PATENT DOCUMENTS

EP        0078685       5/1983
EP        1736119      12/2006
(Continued)

OTHER PUBLICATIONS

International Search Report for PCT/EP2010/065951, Completed by the European Patent Office on Mar. 15, 2011, 3 Pages.

*Primary Examiner* — Diane Yabut
*Assistant Examiner* — Martin T Ton
(74) *Attorney, Agent, or Firm* — Brooks Kushman P.C.

(57) ABSTRACT

A tool for facilitating insertion of a speech valve with a flexible retention flange into a fistula between the trachea and the esophagus of a human patient. The tool has a wall curved to define a passage having opposed open first and second passage ends and an axis extending therebetween. The wall has an external surface insertable into a fistula between the trachea and esophagus and defining a slot which extends from the passage to the external surface of the wall. The slot has an opening at the first passage end extending from the first passage end to at least a part of the way to the second passage end and at least a portion of the slot progresses angularly around the axis.

5 Claims, 9 Drawing Sheets

(51) Int. Cl.
*A61B 17/34* (2006.01)
*A61B 17/24* (2006.01)

(58) Field of Classification Search
CPC .. A61F 2017/00464; A61F 2017/00469; A61F 2017/00473
USPC ............................................. 606/108; 623/9
See application file for complete search history.

(56) References Cited

U.S. PATENT DOCUMENTS

| | | | |
|---|---|---|---|
| 5,800,342 A * | 9/1998 | Lee ..................... | A61B 1/303 600/114 |
| 5,935,165 A * | 8/1999 | Schouwenburg ................ | 623/9 |
| 5,976,151 A | 11/1999 | Siegbahn | |
| 6,776,797 B1 | 8/2004 | Blom et al. | |
| 2001/0002440 A1* | 5/2001 | Bonutti ....................... | 606/232 |
| 2006/0116691 A1* | 6/2006 | Bonacci ....................... | 606/108 |
| 2007/0060801 A1* | 3/2007 | Neinast ........................ | 600/300 |
| 2008/0086168 A1 | 4/2008 | Cahill | |
| 2008/0262432 A1* | 10/2008 | Miller ............ | A61M 25/09041 604/164.13 |
| 2009/0036983 A1 | 2/2009 | Tran | |
| 2009/0102180 A1* | 4/2009 | Karling et al. ................ | 285/20 |
| 2009/0259310 A1* | 10/2009 | Blom ............................. | 623/9 |

FOREIGN PATENT DOCUMENTS

| | | |
|---|---|---|
| EP | 2110101 | 10/2009 |
| GB | 2443164 | 4/2008 |
| WO | 9529649 | 11/1995 |
| WO | 9635399 | 11/1996 |
| WO | 9723341 | 7/1997 |
| WO | 2005097001 | 10/2005 |
| WO | 2005102458 | 11/2005 |
| WO | 2008050093 | 5/2008 |
| WO | 2009140594 | 11/2009 |

* cited by examiner

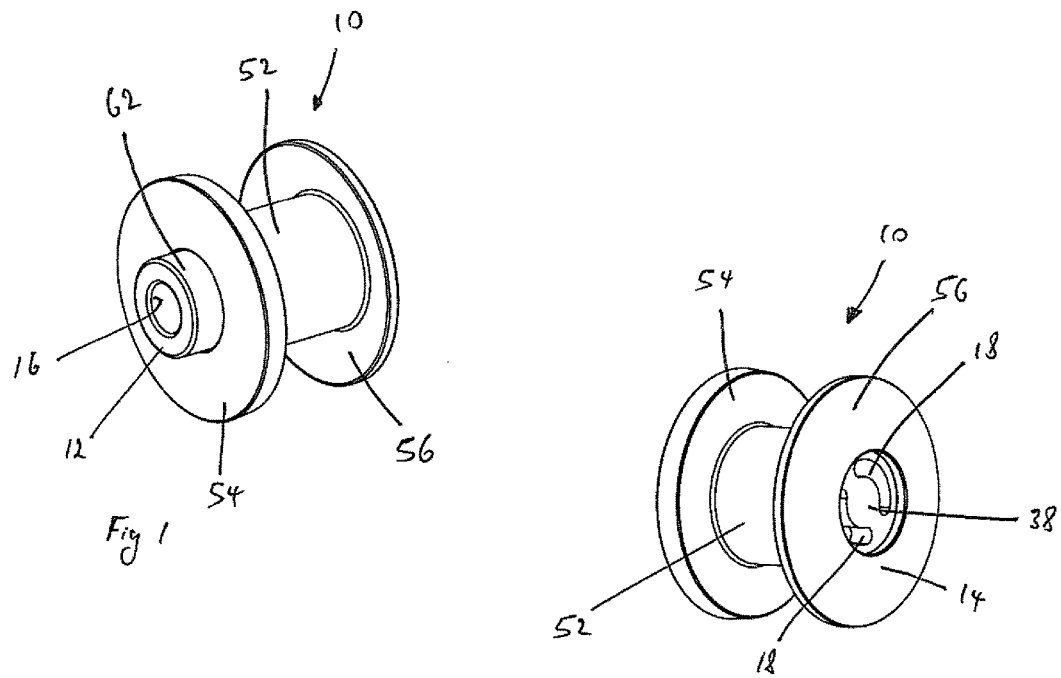
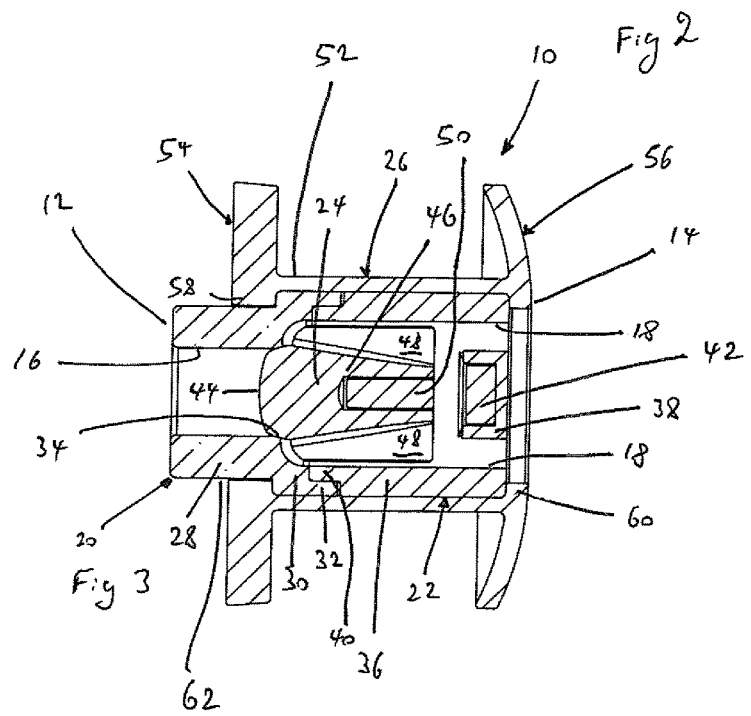

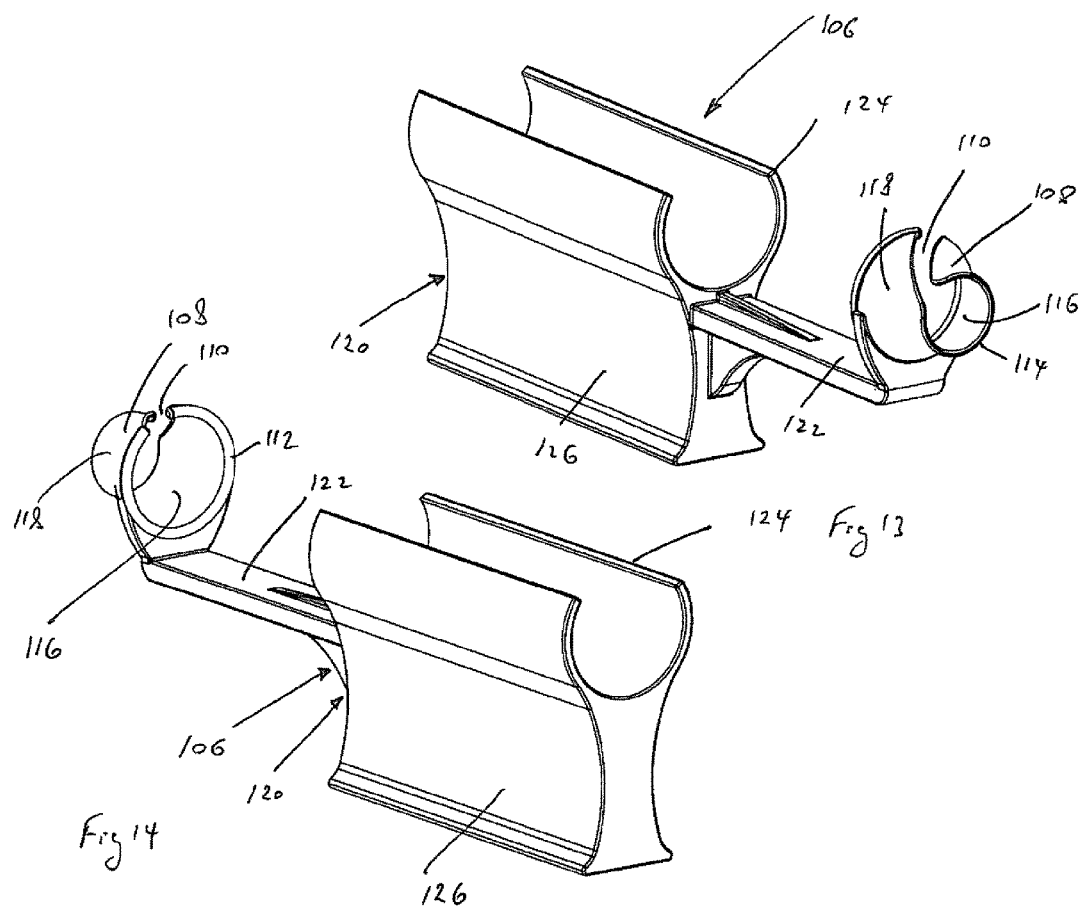
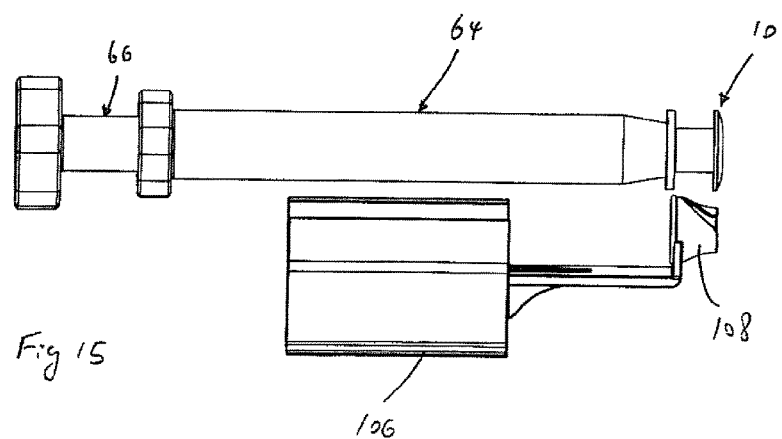

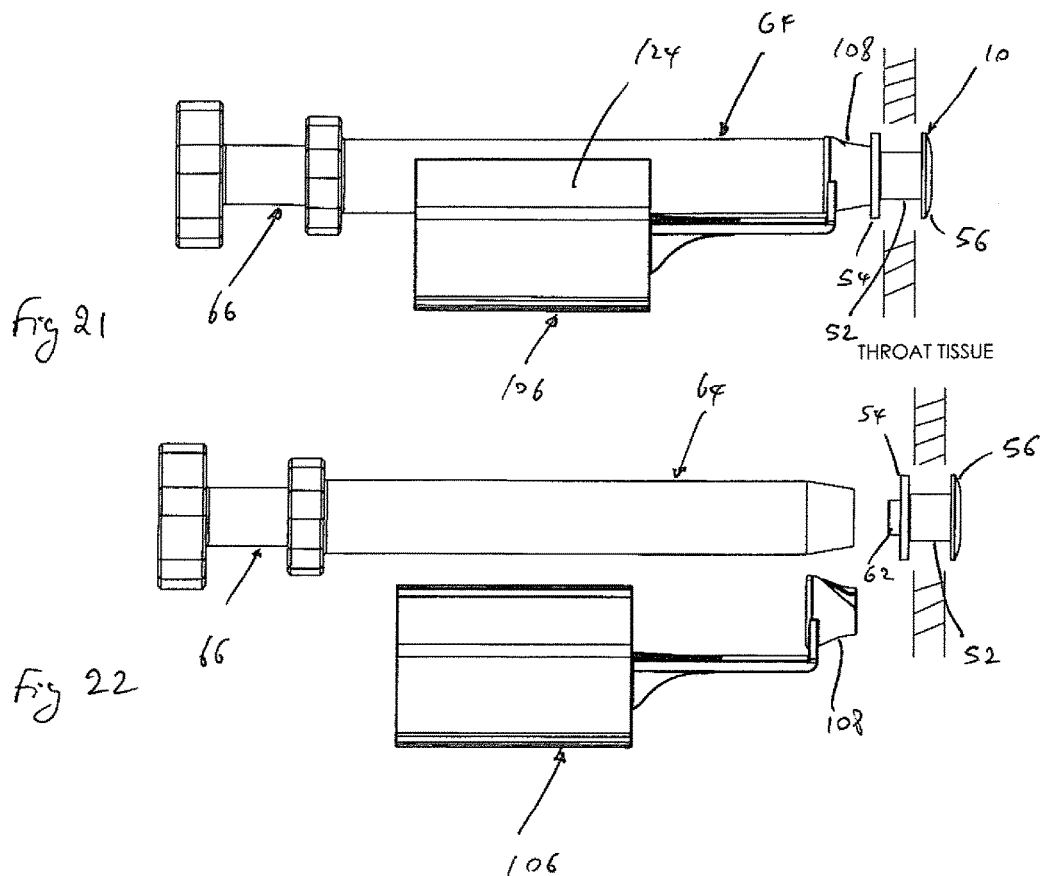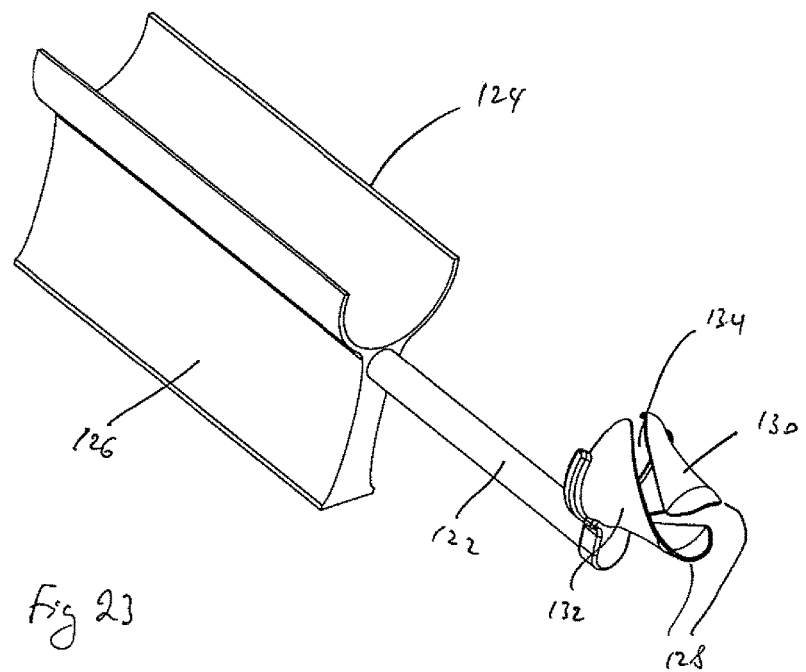

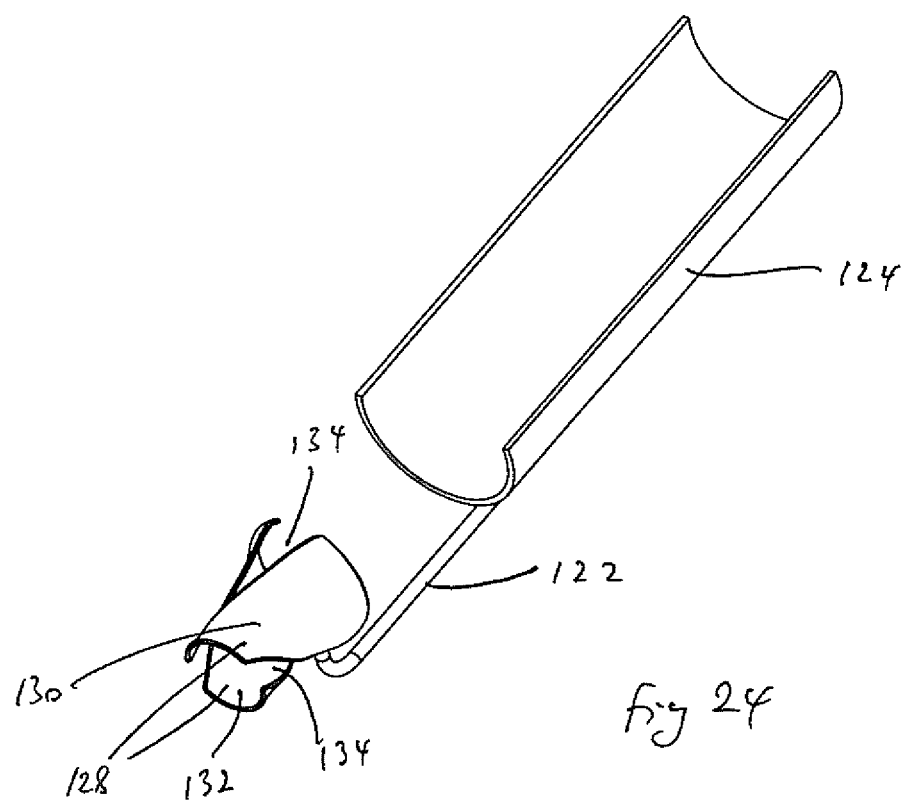

SPEECH VALVE, A TOOL FOR FACILITATING INSERTION OF A SPEECH VALVE AND A TOOL FOR HOLDING A SPEECH VALVE

CROSS-REFERENCE TO RELATED APPLICATION

This application is the U.S. national phase of PCT Appln. No. PCT/EP2010/065951 filed on Oct. 22, 2010, which claims priority to GB Patent Application No. 0918995.2 filed on Oct. 29, 2009, the disclosures of which are incorporated in their entirety by reference herein.

The invention relates to a speech valve. In addition, the invention relates to a tool for facilitating insertion of a speech valve into a fistula between the trachea and the oesophagus of a human patient. Further, the invention relates to a tool for holding a speech valve, which is particularly useful for holding a speech valve during insertion of the speech valve into such a fistula.

Treatment of throat cancer often involves laryngectomy. The laryngectomy results in the trachea being diverted to an external opening, or stoma, located at the throat of a patient. The natural opening between the trachea and the oesophagus is closed so that there is no communication between the trachea and the oesophagus. After such an operation, the patient is unable to talk. In order to allow the patient to recover some vocal function, it is known to surgically create a hole, or fistula, between the trachea and the oesophagus. When the patient desires to talk, the patient covers the stoma at the outside of the throat with a finger so that air from the lungs is directed from the trachea into the oesophagus and speech can be created in a manner which is broadly similar to normal speech.

It is known to provide such a fistula with a speech valve. The speech valve acts as a one way valve which closes to prevent food and liquid passing from the oesophagus into the trachea, but which is opened by air pressure when the stoma at the outside of the throat is covered and the patient is breathing out. In this way, air passes through the speech valve from the trachea into the oesophagus to allow speech.

A known speech valve is disclosed in WO 2008/050093. This speech valve has a tracheal end and an oesophageal end and an axis extending therebetween. The speech valve defines a passage for carrying air from a tracheal opening at the tracheal end to an oesophageal opening at the oesophageal end. A first resilient annular flange extends radially outwardly from the tracheal end and a second resilient annular flange extends radially outwardly from the oesophageal end. In use, the tracheal flange lies within the trachea and restricts movement of the speech valve through the fistula towards the oesophagus. The oesophageal flange lies within the oesophagus and restricts movement of the speech valve through the fistula towards the trachea. In this way, the speech valve is held in place in the fistula.

Because the oesophageal flange is resilient, the speech valve can be inserted through the stoma into the fistula, oesophageal end first, until the oesophageal flange lies within the oesophagus. During this process, the oesophageal flange is flexed towards the axis of the speech valve by contact with the tissue surrounding the fistula before the oesophageal end enters into the oesophagus whereupon the oesophageal flange can spring back to its normal, radially extending position. However, this method can be unreliable because the flange can get caught in the fistula and not open fully. Also the process can be traumatic to the tissue surrounding the fistula, in view of the pressure applied to this tissue by the folded oesophageal flange. This can make insertion of a speech valve unpleasant to the patient undergoing this process.

In an attempt to alleviate this problem, U.S. Pat. No. 5,976,151 discloses a loading tube and a handle that, together, can be used to insert a speech valve into a fistula. The handle has a head which is sized to be received in an opening at the tracheal end of the speech valve. The head is held within the opening by friction and, optionally, the tracheal flange of the speech valve can be provided with a removable string which engages with the handle. The loading tube of U.S. Pat. No. 5,976,151 is a tapering tube having an axially extending slot at the wider end. This tube is used to facilitate insertion of the speech valve into the fistula. In order to do this, the oesophageal flange is folded towards the axis of the speech valve, so that the flange extends axially forward from the oesophageal end of the speech valve. In this configuration, the flange is inserted into the loading tube, followed by the remainder of the speech valve. The speech valve has the handle attached to the tracheal end, as discussed above. The narrow end of the loading tube is then inserted into the fistula, and the speech valve is pushed through the tube and out of the narrow end, whereupon the oesophageal flange resumes its normal, radially extending position, lying within the oesophagus. In this way, trauma to the tissue surrounding the fistula is reduced.

However, given that a speech valve is typically a few millimeters long and a few millimeters wide, it can be very difficult to fold the oesophageal flange while inserting the speech valve into the loading tube. The slot at the wider end of the tube is provided in order to facilitate loading, but the loading process is still difficult.

U.S. Pat. No. 5,935,165 discloses two different tools that can be used for holding a speech valve during insertion of the speech valve into a fistula. One such tool is shown in FIG. 8 of U.S. Pat. No. 5,938,165. This tool has an outer tubular member provided, at its end, with a plurality of flexible fingers. Each finger is provided with a respective cam portion. The holding tool also has a rod which fits within the outer tube. The rod interacts with the cam portions on the fingers and can be used to flex the fingers radially outwardly so that the fingers engage with an annular groove which extends around an opening within the speech valve.

A second tool for holding a speech valve during insertion is shown in FIG. 2 of U.S. Pat. No. 5,935,165. This tool has an outer helical thread that engages with an inner helical thread provided in an opening of the speech valve. However, in use, once the speech valve has been inserted into the fistula using this holding tool, it is difficult to achieve relative rotation between the speech valve and the holding tool so as to disengage the holding tool.

In accordance with a first aspect of the invention there is provided a tool for facilitating insertion of a speech valve with a flexible retention flange into a fistula between the trachea and the oesophagus of a human patient, the tool having a wall curved to define a passage having opposed open first and second passage ends, the wall having an external surface insertable into a fistula between the trachea and the oesophagus, the passage having an axis extending between the first and second passage ends, the wall defining a slot which extends from the passage to the external surface of the wall, the slot having an opening at the first passage end and the slot extending from the first passage end at least part of the way to the second passage end, at least a portion of the slot progressing angularly around the axis as is progresses from the first passage end towards the second passage end.

In accordance with a second aspect of the invention, there is provided a tool for facilitating insertion of a speech valve with a flexible retention flange into a fistula between the trachea and the oesophagus of a human patient, the tool having a tubular wall which defines therein a passage extending between first and second opposed open ends of the tubular wall, the tubular wall having a slot extending from the first wall end at least part of the way to the second wall end and across the tubular wall from the passage to the exterior of the tubular wall, the tubular wall having an axis and at least a portion of the slot progressing angularly around the axis as the slot progresses from the first wall end towards the second wall end.

The facilitating tool of either the first aspect or the second aspect of the invention is used in the following manner. Firstly, a portion of the oesophageal flange of a speech valve is inserted into the slot. Then, the speech valve is rotated relative to the tool so that the slot guides the oesophageal flange into the passage of the tool. In this way, the oesophageal flange is folded towards the axis of the speech valve extending axially outwardly from the oesophageal end of the speech valve. In this way, the oesophageal flange can be brought, relatively easily, into a folded configuration which facilitates insertion of the speech valve into the fistula. The fact that the slot extends angularly around the axis, for example in a spiral configuration, greatly assists in this process.

In accordance with a third aspect of the invention, there is provided a speech valve for insertion into a fistula between the trachea and the oesophagus of a human patient, the speech valve having a tracheal end and an oesophageal end and an axis extending therebetween, the speech valve defining a passage for carrying air from a trachael opening at the tracheal end to an oesophageal opening at the oesophageal end, the speech valve having a radially extending retainer for location in the trachea to restrict movement of the speech valve through the fistula towards the oesophagus, wherein the speech valve is provided at the tracheal end with a tubular portion which extends axially outwardly of the retainer and which provides the trachael opening of the passage.

In accordance with a fourth aspect of the invention, there is provided a tool for holding a speech valve during insertion of the speech valve into a fistula between the trachea and the oesophagus of a human patient, the tool comprising an inner member having a plurality of flexible fingers and an outer sleeve surrounding the inner member, the outer sleeve having an open end and a cam portion, the inner member being moveable relative to the outer sleeve whereupon the inner member interacts with the cam portion to cause the flexible fingers to move into a gripping configuration at or adjacent the open end of the outer sleeve.

The holding tool of the fourth aspect of the invention is preferably adapted to hold the speech valve of the third aspect of the invention. In this case, the tubular portion of the speech valve is inserted into the open end of the outer sleeve of the holding tool and the flexible fingers of the holding tool, in the gripping configuration, grip the tubular portion of the speech valve.

The following is a more detailed description of embodiments of the invention, by way of example, reference being made to the amended schematic drawings in which:

FIG. 1 is a perspective view of a speech valve in accordance with the invention showing a tracheal end of the speech valve;

FIG. 2 is a perspective view of the speech valve of FIG. 1, showing an oesophageal end of the speech valve;

FIG. 3 is a cross-sectional view of the speech valve of FIGS. 1 and 2;

FIG. 13 is a first perspective view of a tool for facilitating insertion of a speech valve;

FIG. 14 is a second perspective view of the facilitating tool of FIG. 13;

FIG. 15 is a perspective view showing together the holding tool of FIGS. 11 and 12, the speech valve of FIGS. 1 to 3 and the facilitating tool of FIGS. 13 and 14;

FIG. 21 is a perspective view of the holding tool, the facilitating tool and the speech valve in a third stage in the insertion of the speech valve into a fistula;

FIG. 22 is a perspective view of the holding tool, the facilitating tool and the speech valve in a fourth stage in the insertion of the speech valve into a fistula;

FIG. 23 shows a first alternative embodiment of the facilitating tool; and

FIG. 24 shows a second alternative embodiment of the facilitating tool.

Figure 4:
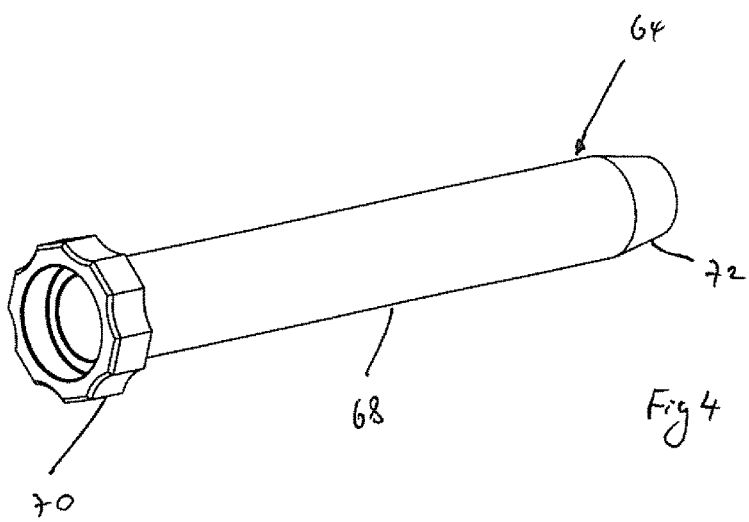
FIG. 4 is a perspective view of an outer sleeve of a holding tool.

Referring to FIGS. 1 to 3, the speech valve 10 has a tracheal end 12 and an oesophageal end 14. A tracheal opening 16 is provided at the tracheal end 12 and an oesophageal opening 18 is provided at the oesophageal end 14. As will be described below in more detail, the tracheal opening 16 is connected to the oesophageal opening 18 by a passage and a valve operates to allow air to pass from the tracheal opening 16 through the passage to the oesophageal opening 18, and to prevent passage of fluid from the oesophageal opening 18 through the passageway to the tracheal opening 16.

As seen in FIG. 3, the speech valve 10 comprises a first body portion 20, a second body portion 22, a closure member 24 and a silicone sleeve 26.

The first body portion 20 has a cylindrical tubular body 28 which, at one end, is provided with an annular shoulder portion 30. An axially extending annular flange 32 extends from the shoulder portion 30. The first body portion 20 is also provided with a valve seat region 34 adjacent the shoulder portion 30.

The second body portion 22 has a cylindrical tubular body 36 which is provided at one end with a integral cross-brace 38 and which is provided at the other end with an axially extending annular flange 40. The cross-brace 38 holds a magnet 42.

The closure member 24 has a sealing head 44 and a stem 46. A plurality (for example 3 as shown in FIG. 3) of fins 48 extend radially outwardly from the stem 46. The fins 48 are spaced angularly from one another around the stem 46 so that gas can pass between the fins 48. A magnet 50 is held within an opening in the stem 46.

As shown in FIG. 3, the axially extending flange 32 of the first body portion 20 is engaged with the axially extending flange 40 of the second body portion 22 so as to provide a fluid tight seal between the first and second body portions 20, 22. The axes of the first and second body portions 20, 22 lie in line with one another and fall on a common axis of the speech valve 10 which passes through the tracheal end 12 and the oesophageal end 14. The closure member 24 is held within the first body portion 20 and the second body portion 22. The closure member 22 is orientated so that the sealing head 44 can seal against the valve seat 34 of the first body portion 20. The outer edges of the fins 48 lie closely and slidingly within the inner surface of the cylindrical tubular body 36 of the second body portion 22. In this way, the closure member 24 can slide between the closed position shown in FIG. 3 to an open position in which the closure member 24 is displaced towards the cross-brace 38. The magnets 42, 50 repel one another and urge the closure member 24 into the closed position shown in FIG. 3.

The first body portion 20, the second body portion 22 and the closure member 24 are preferably formed from a relatively rigid material, such as a ceramic material. One suitable ceramic material is partially stabilised zirconia.

The silicone sleeve 26 has a central cylindrical portion 52. At one end of the cylindrical portion 52, an annular tracheal flange 54 extends radially outwardly. At the other end of the cylindrical portion 52, an annular oesophageal flange 56 also extends radially outwardly. As seen in FIG. 3, the oesophageal flange 56 has an inwardly facing concave surface and an outwardly facing convex surface. In addition, the tracheal flange 54 includes an annular tracheal lip portion 58 which extends radially inwardly. The oesophageal flange 56 includes an annular oesophageal lip portion 60 which extends radially inwardly. As seen in FIG. 3, the cylindrical portion 52 of the silicone sleeve 26 fits tightly over the outer surface of the second body portion 22 and also tightly over the outer surface of the shoulder portion 30 of the first body portion 20. The tracheal lip portion 58 engages with the shoulder portion 30 of the first body portion 20. The oesophageal lip portion 60 engages with the free end of the second body portion 22. In this way, the silicone sleeve 26 is held firmly in place in relation to the first and second body portions 20, 22.

As seen in FIGS. 1 and 3, a tubular projecting portion 62 of the first body portion 20 extends axially outwardly from the tracheal flange 54, 58. This tubular projecting portion 62 serves a purpose described below.

The first body portion 20 and the second body portion 22 together form a rigid body of the speech valve 10 which helps to maintain the shape of the speech valve and with which the tubular projecting portion 62 is integral.

It will be appreciated that the speech valve 10 need not be as described above. Any suitable configuration may be used which has a tubular projecting portion extending axially outwardly from a tracheal retention flange. In addition, the tracheal retention flange 54 may have any configuration suitable to help retain the speech valve in the fistula—for example it need not be annular. It will also be appreciated that any suitable mechanism for opening and closing the speech valve 10 may be used. The use of a sliding closure member is not necessary.

Figure 5:
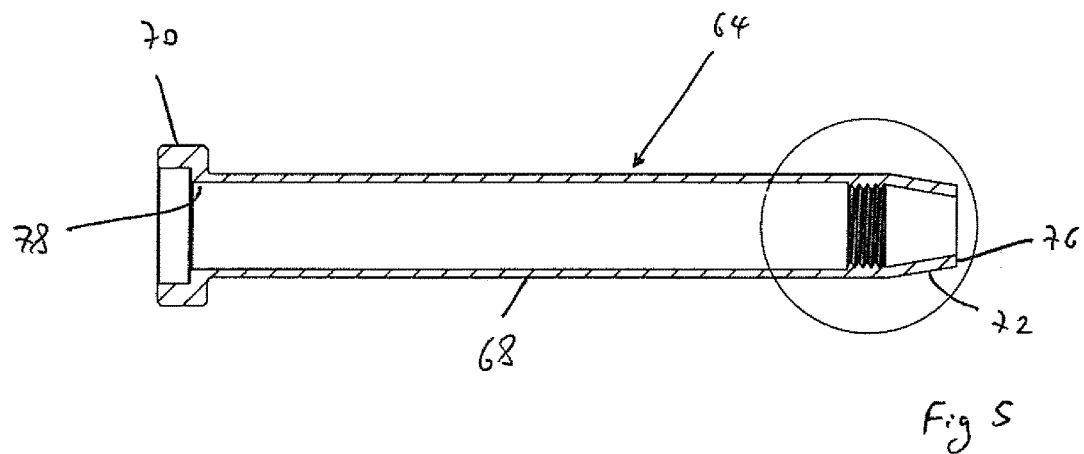
FIG. 5 is a cross-sectional view of the outer sleeve of FIG. 4.
Figure 6:
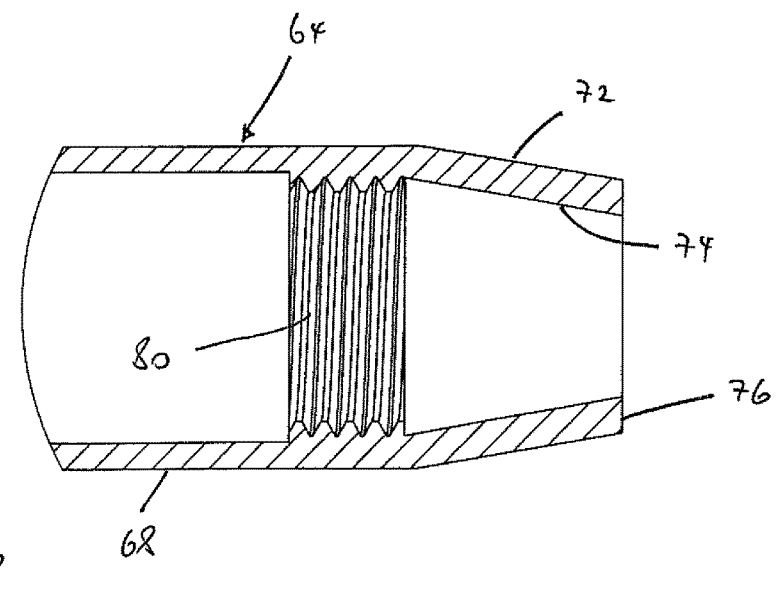
FIG. 6 is an enlarged cross-sectional view of part of the outer sleeve of FIGS. 4 and 5.
Figure 7:
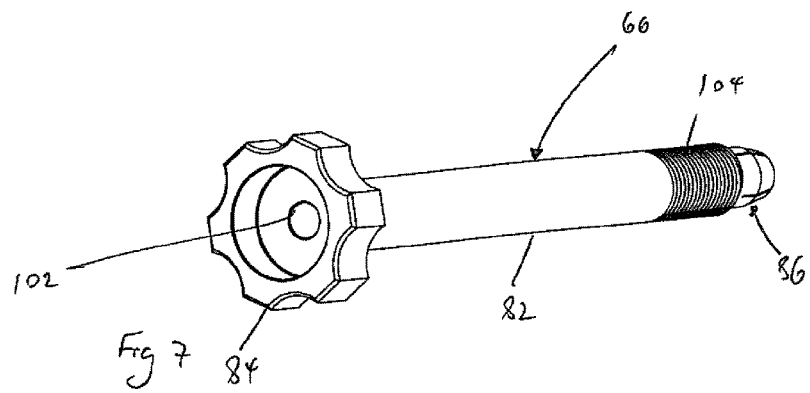
FIG. 7 is a perspective view of an inner member of the holding tool.

During insertion of the speech valve 10, the speech valve 10 is conveniently held using a holding tool consisting of an outer sleeve 64 as shown in FIGS. 4 to 6 and an inner member 66 as shown in FIGS. 7 to 10. The outer sleeve 64 and the inner member 66 will now be described.

As best seen in FIGS. 4 to 6, the outer sleeve 64 of the holding tool is tubular. The outer sleeve 64 has a cylindrical central portion 68. At one end of the central portion 68 is a knurled handle portion 70. The knurling of the handle portion 70 facilitates rotation of the outer sleeve 64. At the other end of the central cylindrical portion 68 is a tapering end portion 72.

As best seen in FIG. 6, the tapering end portion 72 has an internal tapering surface 74 which narrows as it extends from the central portion 68 to a first open end 76.

A second open end 78 is provided at the handle portion 70. The interior of the outer sleeve 64 forms a fluid tight passage between the first and second open ends 76, 78.

A screw thread 80 is provided at an inner surface of the central cylindrical portion 68, adjacent the tapering end portion 72.

The inner member 66 is best seen in FIGS. 7 to 10. The inner member 66 is also tubular and has a central cylindrical portion 82. At one end of the central cylindrical portion 82 is a handle portion 84 which is knurled to facilitate rotation of the inner member 66.

Figure 8:
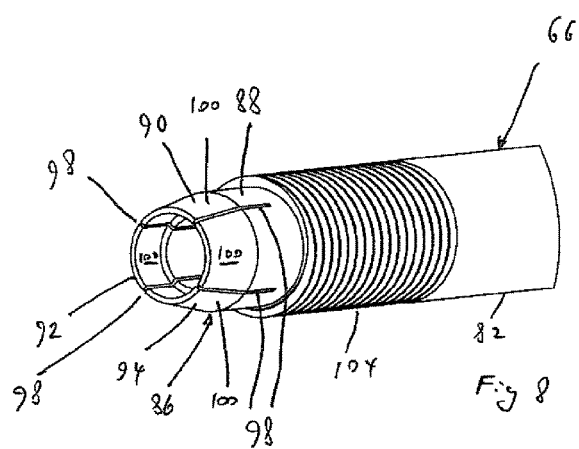
FIG. 8 is an enlarged perspective view of part of the inner member shown in FIG. 7.
Figure 9:
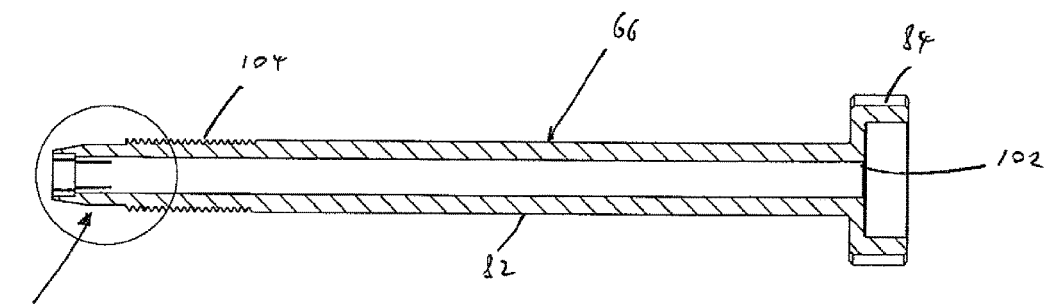
FIG. 9 is a cross-sectional view of the inner member of FIGS. 7 and 8.
Figure 10:
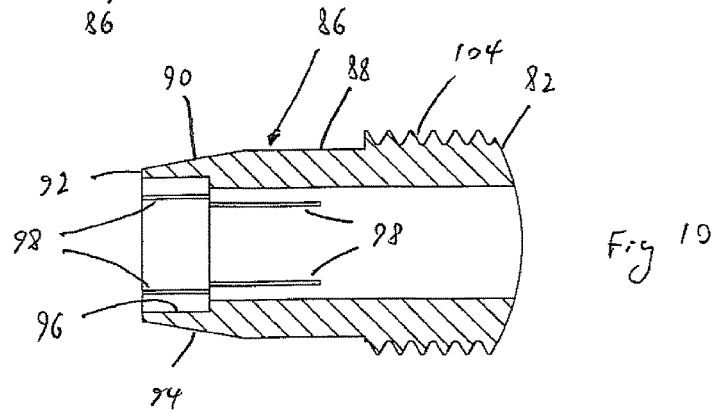
FIG. 10 is an enlarged cross-sectional view of part of the inner member of FIGS. 7 to 9.

At the other end of the central cylindrical portion 82 is an end gripping portion 86. The end gripping portion 86 is best seen in FIGS. 8 and 10. The end gripping portion 86 has a cylindrical region 88 which lies immediately adjacent to the central cylindrical portion 82. It will be noted that the wall of the cylindrical region 88 is thinner than the wall of the central cylindrical portion 82. This allows the wall of the end gripping portion 86 to be more flexible, for a purpose to be described below. The end gripping portion also includes a tapering region 90 which extends from the cylindrical region 88 to a first open end 92. The tapering region 90 has a tapering outer surface 94 which narrows as it extends from the cylindrical region 88 to the first open end 92. Additionally, the tapering region 90 is formed with an internal rebate 96 which extends inwardly from the first open end 92.

As best seen in FIG. 8, four angularly spaced slots 98 extend axially into the end gripping portion 86 from the first open end 92. The slots 98 divide the end gripping portion 86 into four fingers 100. Each finger lies between a respective pair of the slots 98. In view of the reduced thickness of the wall of the cylindrical region 88, the fingers 100 can be flexed inwardly or outwardly.

The inner member 66 also has a second open end 102 which is provided in the handle portion 84. The interior of the inner member 66 provides a fluid tight passage (with the exception of the slots 98) which extends from the first open end 92 to the second open end 102. A screw thread 104 is provided on the external surface of the central cylindrical portion 82, adjacent the end gripping portion 86.

Figure 11:
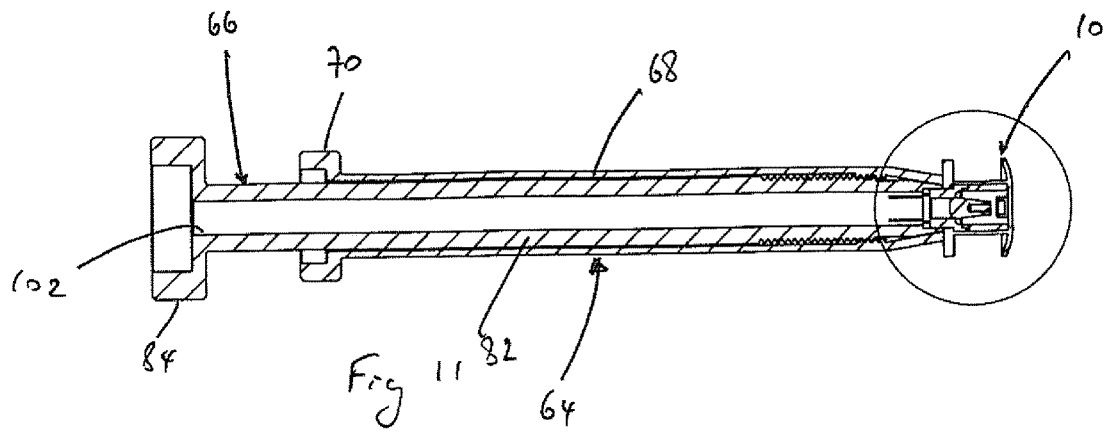
FIG. 11 is a cross-sectional view of the outer sleeve of FIGS. 4 to 6 assembled with the inner member of FIGS. 7 to 10 so as to form the holding tool, the holding tool holding the speech valve of FIGS. 1 to 3.
Figure 12:
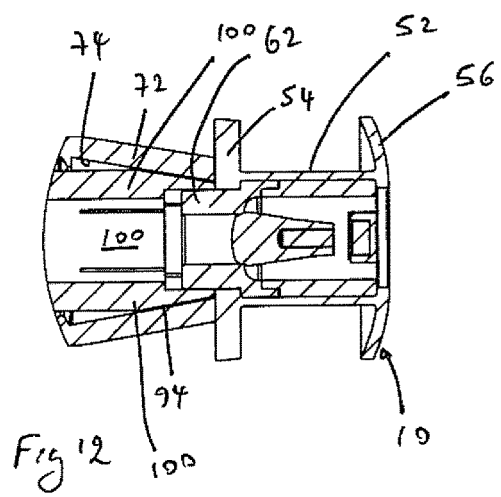
FIG. 12 is an enlarged cross-sectional view of part of FIG. 11 showing the speech valve being held by the holding tool.
Figure 16:
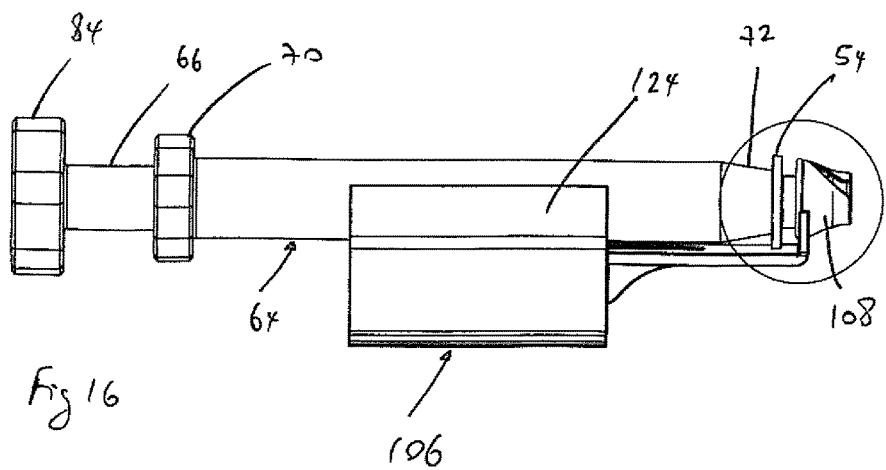
FIG. 16 is a perspective view showing the holding tool, the facilitating tool and the speech valve, in a first stage in the insertion of the speech valve into a fistula.
Figure 17:
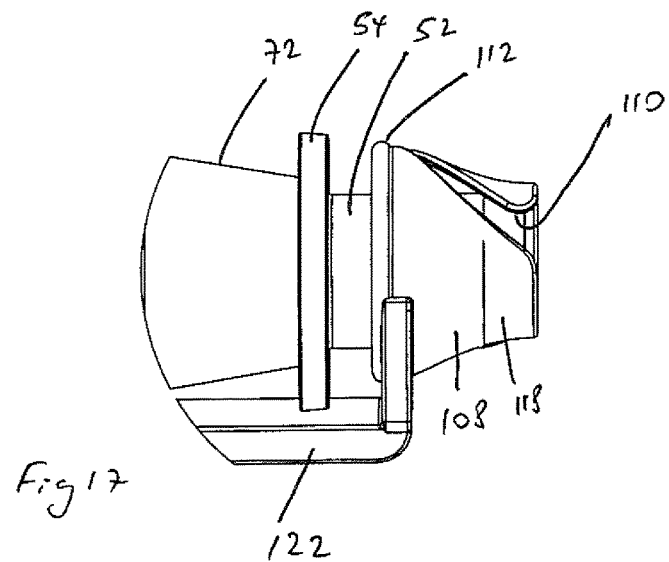
FIG. 17 is an enlarged portion of FIG. 16.

As best seen in FIGS. 11 and 12, the holding tool is assembled by inserting the inner member 66 into the outer sleeve 64 so that the screw thread 80 of the outer sleeve 64 engages the screw thread 104 of the inner member 66. As seen in FIG. 11, the two handle portions 70, 84 lie at the same end of the holding tool.

As best seen in FIG. 12, the tapering outer surface 94 of the inner member 66 lies within and contacts the tapering internal surface 74 of the outer sleeve 64. When the inner member 66 is rotated relative to the outer sleeve 64, so that the screw thread engagement advances the inner member 66 towards the first open end 76 of the outer sleeve 64, the fingers 100 cam against the internal tapering surface 74 of the outer sleeve so that the fingers 100 are flexed radially inwardly. When the inner member 66 is rotated in the other sense, relative to the outer sleeve 64, the inner member 66 moves towards the second open end 78 of the outer sleeve 64 whereupon the fingers 100 flex back outwardly to their original positions.

As best seen in FIG. 11, the outer sleeve 64, together with the inner member 66, form a fluid tight passage which extends from the second open end 102 of the inner member 66 to the first open end 76 of the outer sleeve 64. This arrangement serves a purpose to be described below.

As seen in FIGS. 11 and 12, the holding tool is adapted for holding the speech valve described above with reference to FIGS. 1 to 3. In order for the holding tool to hold the speech valve 10, the tubular projecting portion 62 of the speech valve 10 is introduced into the end gripping portion 86 of the inner member 66. As best seen in FIG. 12, the tubular projecting portion 62 of the speech valve 10 is received in the internal rebate 96 of the end gripping portion 86 of the inner member 66. The tubular projecting portion 62 is inserted into the holding tool until the first open end 76 of the outer sleeve 64 abuts the resilient tracheal flange 54, 58. The first open end 76 may also contact the tracheal lip 58 which forms part of the tracheal flange 54. The inner member 66 is then rotated relative to the outer sleeve 64 so as to advance the inner member 66 towards the first open end 76 of the outer sleeve 64. As described above, this causes the fingers 100 to be flexed inwardly (by interaction with the camming tapering internal surface 74). In this way, the fingers 100 grip tightly the tubular projecting portion 62 of the speech valve 10.

Additionally, as the first open end 76 of the outer sleeve 64 of the holding tube contacts the resilient tracheal flange 54 there is formed a relatively fluid tight seal between the speech valve 10 and the holding tool such that the internal passage of the holding tool is in fluid communication with the internal passage of the speech valve 10.

The apparatus also includes a tool for facilitating insertion of the speech valve 10 into a fistula between the trachea and the oesophagus of a human patient. This facilitating tool 106 is best seen in FIGS. 13 and 14.

The facilitating tool 106 comprises a wall 108 which, as seen in FIGS. 13 and 14, curves round so as to form generally a funnel shape or a tapering tube shape which is interrupted by a slot 110 that will be described in more detail below. The funnel-shaped wall 108 has a wider open end 112 and an opposite narrower open end 114.

The wider end 112 and the narrower end 114 are rounded so as to provide smooth edges. The funnel-shaped wall 108 also defines an internal passage 116 which extends from the wider end 112 to the narrower end 114.

The funnel-shaped wall 108 is formed of a flexible material. Flexible plastics materials are suitable. One example of a suitable plastics material is Hytrel. Other thermoplastic elastomers may be used.

The slot 110 extends the full length of the funnel-shaped wall 108 and has a first opening at the wider end 112 and a second opening at the narrower end 114. The slot 110 also extends between the internal passage 116 to an external surface 118 of the wall 108.

The internal passage 116 has an axis that extends through the wider end 112 and the narrower end 114. As shown in FIGS. 13 and 14, as the slot 110 extends in an axial direction from the wider end 112 to the narrower end 114 it also progresses angularly around the axis. In the current embodiment, the slot 110 has a generally spiral configuration.

The facilitating tool 106 has a handle generally shown at 120. The handle 120 comprises a connecting portion 122 which is attached to the wider end 112 of the funnel-shaped wall 108. In turn, the connecting portion 122 connects to a clip portion 124 which is semi-cylindrical in shape and resilient so as to allow the clip portion 124 to be clipped around a tube of appropriate diameter. Adjacent to the clip portion 124 is a holding portion 126 which allows the facilitating tool 106 to be easily gripped by an operator.

The operation of the holding tool, the facilitating tool and the speech valve will now be described with reference in particular to FIGS. 11, 12 and 15 to 22. In general terms, the holding tool is used to hold the speech valve 10 while the facilitating tool 106 is used to flex the oesophageal flange 56 into a configuration suitable for insertion into a fistula between the trachea and the oesophagus of a human patient.

Firstly, the holding tool, with the inner member 66 engaged within the outer sleeve 64 is attached to the speech valve 10. As discussed above, this involves insertion of the tubular projecting portion 62 into the end gripping portion 86 of the inner member 66 and clamping of the resilient fingers 100 around the tubular projecting portion 62 so as to grip the speech valve 10 tightly. The fact that the holding tool firmly grips the tracheal end 12 of the speech valve 10 facilitates manipulation of the speech valve 10, which may be only a few millimeters in length and only a few millimeters in width.

Once the holding tube has been clamped around the tubular projecting portion 62 of the speech valve 10, the arrangement is that shown in FIGS. 11 and 15. At this point, it would be possible to insert the speech valve 10 and the holding tool through a stoma at the outside of the throat of a patient and simply push the speech valve into a fistula between the trachea and the oesophagus. However, as discussed above, as the outer diameter of the oesophageal flange 56 is greater than the inner diameter of the fistula, this would involve flexing of the oesophageal flange 56 by contact between the oesophageal flange 56 and the wall of the fistula. This is undesirable because it applies a significant force to the wall of the fistula and can cause significant trauma to the soft tissue surrounding the fistula.

In order to alleviate this problem, the facilitating tool 106 is used to flex the oesophageal flange 56 into a suitable configuration so as to facilitate insertion of the speech valve 10 into the fistula. This is performed as follows.

Firstly, by holding the facilitating tool 106 at an angle to the holding tool, a portion of the oesophageal flange 56 is inserted into the slot 110, entering the slot 110 at the slot opening at the wider end 112 of the funnel-shaped wall 108. The facilitating tool 106 is then brought generally parallel to the holding tool. At this stage, the holding tool is rotated in a clockwise direction relative to the facilitating tool 106 (clockwise when looking onto the handle portion 84 of the inner member 66). It will be noted that the slot 110 progresses in a clockwise direction around the wall 108 as the slot extends from the wider end 112 to the narrower end 114.

(It will be noted that when the holding tool is rotated, there is no relative rotation between the outer sleeve 64 and the inner member 66.)

Because the speech valve 10 is held tightly by the holding tool, the speech valve 10 also rotates. The operator, in addition to rotating the holding tool, also holds the holding portion 126 of the facilitating tool 106, keeping the facilitating tool 106 motionless. The relative rotation between the oesophageal flange 56 and the funnel-shaped wall 108 tends to wind the oesophageal flange 56 into the slot 110 while the slot 110 acts to fold the oesophageal flange 56 into the passage 116 within the funnel-shaped wall 108. This folding is assisted by the funnel shaped profile of the wall 108.

Figure 18:
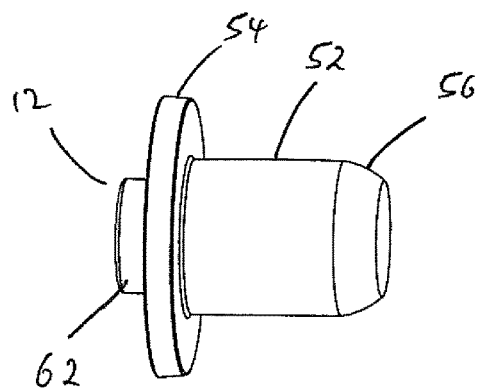
FIG. 18 is a perspective view of the speech valve of FIGS. 1 to 3 showing an oesophageal flange of the speech valve held in a folded position, as it would be held by the facilitating tool of FIGS. 13 and 14.

After sufficient relative rotation between the speech valve 10 and the facilitating tool 106, the oesophageal flange 56 is contained fully within the passage 116, and is folded towards the axis of the speech valve and axially outwardly of the oesophageal end 14 of the speech valve 10. This configuration of the speech valve 10 is shown in FIG. 18 with the facilitating tool 106 removed for illustration so as to allow the configuration of the oesophageal flange 56 to be seen. (Of course, if the oesophageal flange 56 was removed from the funnel-shaped wall 108 in practice, the oesophageal flange 56 would revert back into its normal, radially extending configuration.)

At the same time as the speech valve 10 is rotated relative to the facilitating tool 106, the holding tool is also advanced a small amount in an axial direction, relative to the facilitating tool 106, so as to push the speech valve 10 into the passage 116 within the funnel-shaped wall 108. This gives rise to the configuration shown in FIGS. 16 and 17.

If the clip portion 124 is not already clipped around the outer sleeve 64 of the holding tool, it may now be clipped in this manner so as to anchor the facilitating tool 106 to the holding tool.

The surgeon then advances the complete assembly, consisting of the holding tool, the speech valve 10 and the facilitating tool 106 through the stoma at the outside of the throat of the patient so that the speech valve 10 enters into the trachea. The surgeon then aligns the funnel-shaped wall 108 of the facilitating tool 106 with the fistula and inserts the wall 108 into the fistula whereupon the external surface 118 of the funnel-shaped wall 108 lies against the soft tissue surrounding the fistula.

Figure 19:
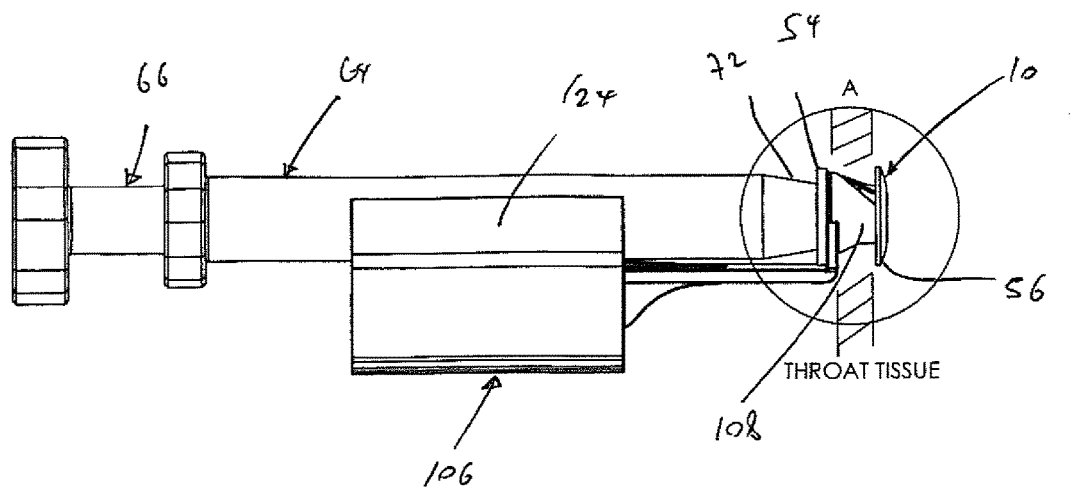
FIG. 19 is a perspective view of the holding tool, the facilitating tool and the speech valve in a second stage in the insertion of the speech valve into a fistula.
Figure 20:
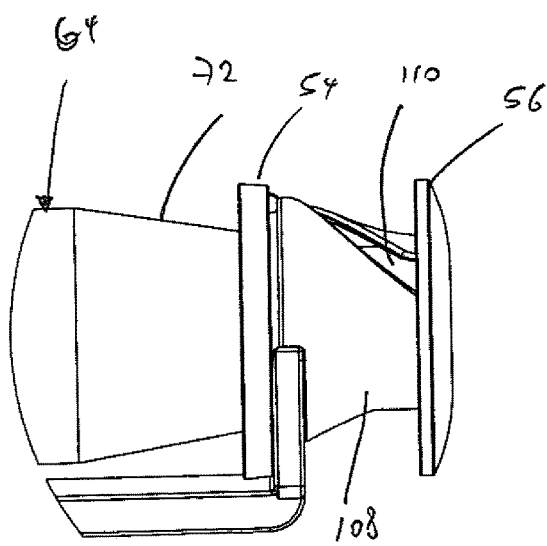
FIG. 20 is an enlarged portion of FIG. 19.

At this stage, the surgeon advances the holding tool relative to the facilitating tool 106 so that the speech valve 10 moves towards the narrow end 114 of the funnel-shaped wall 108. As will be appreciated, as the oesophageal flange 56 passes out through the narrower end 114 of the funnel-shaped wall 108, the oesophageal flange begins to resume its normal, radially extending configuration (as shown in FIGS. 1 to 3). This stage is shown in FIGS. 19 and 20. The oesophageal flange 56 now lies within the oesophagus so that the concave, axially inwardly facing surface of the flange 56 faces or contacts the wall of the oesophagus. This helps to retain the speech valve 10 in the fistula and resists passage of the speech valve 10 into the trachea.

The surgeon then pulls the facilitating tool 106 back towards the handle portion 70 of the outer sleeve 64. During this movement, the funnel-shaped wall 108 (which as stated above is made of a flexible material) increases in diameter with a concomitant increase in the width of the slot 110. Simultaneously, the tracheal flange 54 flexes against the tapering end portion 72 of the outer sleeve 64. Eventually, the tracheal flange 54 passes through the narrower end 114 of the funnel-shaped wall 108 and flexes back to its normal radially extending configuration. This stage is shown in FIG. 21. The tracheal flange 54 helps to retain the speech valve 10 in the fistula and prevents the speech valve dislodging into the oesophagus.

At this stage, the facilitating tool 106 can be pulled off the holding tool completely, removed from the stoma, and is no longer required. The holding tool is then disengaged from the speech valve 10 by rotating the inner member 66 relative to the outer sleeve 64. This releases the fingers 100 from the tubular projecting portion 62 so that the tubular projecting portion 62 can be withdrawn from the first open end 76 of the outer sleeve 64. This stage is shown in FIG. 22. The speech valve 10 is now properly inserted within the fistula and the holding tool can be withdrawn from the trachea through the stoma.

The apparatus discussed above has several advantageous features.

Firstly, the provision of the tubular projecting portion 62 on the speech valve 10 is advantageous during every-day use of the speech valve 10. Because the projecting portion 62 projects slightly into the trachea, this helps to prevent any fluid in the trachea from entering into the speech valve 10.

In addition, the provision of the tubular projecting portion 62 allows the speech valve 10 to be gripped firmly and securely by the holding tool.

In addition, the use of the tubular projecting portion 62 as the portion that is gripped by the holding tool, makes it possible to use the holding tool to withdraw the speech valve 10 from the fistula. In order to do this, the holding tool is passed through the stoma into the trachea. The holding tool is then manipulated until the tubular projecting portion 62 enters into the first open end 76 of the outer sleeve 64. The holding tool is then tightened around the tubular projecting portion 62 as discussed above. Once the speech valve 10 is firmly held by the holding tube in this way, the holding tube can be used to withdraw the speech valve 10 from the fistula. In current clinical practice, a speech valve is normally removed from a fistula simply by gripping it with a pair of forceps and pulling. However, the ability to attach the holding tube in a firm and secure manner to the speech valve 10 facilitates the removal process.

As discussed above, U.S. Pat. No. 5,976,151 and U.S. Pat. No. 5,935,165 disclose various holding tools that can be used to hold speech valves. However, in each case, the tool is inserted into an end of the speech valve and engages with an inner surface, sometimes a groove, in the speech valve. In practice, it is very difficult indeed to use such a tool in order to remove a speech valve from a fistula. This is because the tool has to be inserted from the stoma across the trachea to the speech valve, and then into a very small opening in the end of the speech valve. Moreover, the speech valve may not be angled in direct alignment with the stoma which makes it difficult to insert such a tool into the end of the speech valve. Additionally, the use of a groove in the internal opening of the speech valve, as shown in FIG. 8 of U.S. Pat. No. 5,935,165, is undesirable because it may facilitate the build up of biofilm. On the other hand, the provision of a tubular projection 62 at the tracheal end 12 of a speech valve 10, and the use of a holding tool that clamps around such a projection 62, greatly facilitates the act of connecting the tool to the speech valve 10 while the speech valve 10 is in situ in the fistula.

As discussed above, the holding tool defines a fluid tight passage extending from the second open end 102 of the inner member 66 to the first open end 76 of the outer sleeve 64. As also discussed above, when the tubular projecting portion 62 is clamped within the first open end 76 so that the first open end 76 abuts the tracheal flange 54, there is a relatively fluid tight joint between the speech valve and the holding tool. The passage through the holding tool is in fluid communication with the passage through the speech valve. In this way, the holding tool can also be used to flush out the speech valve with water or saline solution while the speech valve is in situ in the fistula. In order to do this, the holding tool is first connected to the tubular projecting portion 62 of the speech valve 10, as discussed above. Water or saline is then introduced into the second open end 102 of the inner member 66.

Water passes through the passage through the holding tool into the tracheal opening 16 of the speech valve 10 and through the speech valve passage, exiting the speech valve passage through the oesophageal opening 18. Such flushing is very useful as it can help to remove food fragments or other detritus which might become lodged within the passage of the speech valve 10.

While, in theory, it may be possible to perform this type of operation using a holding tool that inserts into an opening at the end of a speech valve, in practice it would be very difficult indeed to flush a speech valve using such a holding tool. Firstly, any internal passage through the holding tool would have to have a very narrow bore and this would restrict flow of liquid through the holding tool. Secondly, considering the holding tool shown in FIG. 8 of U.S. Pat. No. 5,935,165, the fingers are provided in an external sleeve and are operated by an internal rod. It would be difficult to produce such a holding tool so as to provide a fluid tight passage extending all the way to the speech valve.

The facilitating tool 106 greatly facilitates insertion of the speech valve 10 into the fistula. As discussed above, it is known from U.S. Pat. No. 5,976,151 to provide a loading tube which is used to hold an oesophageal flange into a forwardly extending folded position. This is shown, for example, in FIG. 3 of U.S. Pat. No. 5,976,151. However, in practice, it proves very difficult to insert the oesophageal flange into the loading tube in the correct folded configuration. On the other hand, the slot 110 provided in the funnel-shaped wall 108 of the facilitating tool 106 allows the oesophageal flange 56 to be folded into the correct orientation within the passageway 116. This is because the configuration of the slot 110, which progresses angularly around the wall 108, allows the oesophageal flange 56 to be "wound" into the passage 116 within the funnel-shaped wall 108.

It will be appreciated that the holding tool and the facilitating tool 106 need not be as described above.

The holding tool may have any configuration such that it has an end suitable for gripping the outer surface of the tubular projecting portion 62 of the speech valve 10. Where it is not required to flush the speech valve 10, using the holding tool, it is not necessary to use inner and outer tubular members 64, 66 so as to define a passageway through the holding tool.

The facilitating tool 106 need also not be as described above. For example, the funnel-shaped wall 108 may potentially be formed with a much lesser degree of taper, or perhaps with no taper at all. In addition, it may not be necessary for the slot 110 to extend all of the way to the narrow end 114 (or to a corresponding outer end in the case that the wall 108 does not have any taper). The slot 110 could progress angularly in a counter-clockwise sense rather than in the clockwise sense described above.

The handle 120 need not be as described above.

Two alternative embodiments of the facilitating tool are shown in FIGS. 23 and 24. In these Figures, features of the alternative embodiments which are similar to the corresponding features of the facilitating tool 106, are given the same reference numerals as the corresponding features and are not described in detail.

In both of the tools shown in FIGS. 23 and 24, the funnel-shaped wall 108 is replaced by a wall 128 which has two discontinuous portions 130, 132 separated by two generally spiral slots 134.

In the alternative embodiment shown in FIG. 24, the handle is provided with a clip portion 124 but the holding portion 126 is omitted. In this case, the operator can simply hold onto the clip portion 124.

The alternative embodiment shown in FIGS. 23 and 24 operate in a similar manner to the facilitating tool 106 described above.

The invention claimed is:

1. An apparatus comprising a speech valve for insertion into a fistula between a trachea and an esophagus of a human patient and a tool for holding the speech valve during insertion of the speech valve into the fistula, the speech valve comprising:

a speech valve body having a tracheal end and an esophageal end and having an axis extending between the tracheal end and the esophageal end, the speech valve body defining a passage for carrying air from a tracheal passage opening at the tracheal end to an esophageal passage opening at the esophageal end, a radially extending retainer for location in the trachea to restrict movement of the speech valve through the fistula towards the esophagus, and the speech valve body having a tubular portion at the tracheal end, the tubular portion extending axially outwardly of the retainer and providing the tracheal passage opening, the tool comprising:

an elongate inner member having a central axis and a tapered distal end formed by a plurality of flexible fingers, and an elongate outer sleeve surrounding the inner member, the outer sleeve having an open distal end and an annular inner cam portion located adjacent the open distal end, wherein the plurality of flexible fingers of the tapered end of the inner member comprising a tubular wall and having a plurality of mutually spaced slots extending axially inwardly from an open end of the tubular wall, each flexible finger being formed by a respective portion of the tubular wall of the inner member lying between a respective pair of adjacent slots, the inner member being axially moveable relative to the outer sleeve whereupon the plurality of flexible fingers interact with the cam portion to cause the flexible fingers to move radially inward into a gripping configuration at the open end of the outer sleeve, the cam portion of the outer sleeve being a tapering inner surface portion which narrows as it progresses towards the open end of the outer sleeve, the flexible fingers lying within the tapering surface portion and being compressed into said gripping configuration by engagement with the tapering surface portion as the inner member is moved towards the open end of the outer sleeve, wherein the holding tool is adapted to hold the speech valve with the tubular portion of the speech valve inserted into the open distal end of the outer sleeve and the flexible fingers in said gripping configuration gripping the tubular portion of the speech valve.

2. The apparatus according to claim 1, wherein the flexible fingers lie fully within the outer sleeve when the flexible fingers are in the gripping configuration.

3. The apparatus according to claim 1, wherein the outer sleeve and the inner member are provided with respective inter-engageable screw threads, so that when the screw threads are engaged the inner member can be moved axially towards and away from the open end of the outer sleeve by relative rotation between the inner member and the outer sleeve in the respective appropriate sense.

4. The apparatus according to claim 1, wherein the holding tool has an inlet and defines a fluid tight passage from the inlet to the open end of the outer sleeve.

5. The apparatus according to claim 4, wherein the inner member comprises a tubular wall and has a plurality of mutually spaced slots extending axially inwardly from an open end of the tubular wall, each flexible finger being formed by a respective portion of the tubular wall lying between a respective pair of adjacent slots, wherein the inlet is provided at an end of the tubular wall of the inner member that is opposite to said open end of the tubular wall.

* * * * *